(12) United States Patent
During

(10) Patent No.: US 11,690,829 B2
(45) Date of Patent: Jul. 4, 2023

(54) USE OF GABOXADOL FOR THE TREATMENT OF NON-24 HOUR SLEEP-WAKE DISORDER

(71) Applicant: Ovid Therapeutics Inc., New York, NY (US)

(72) Inventor: Matthew During, Weston, CT (US)

(73) Assignee: Ovid Therapeutics Inc., New York, NY (US)

( * ) Notice: Subject to any disclaimer, the term of this patent is extended or adjusted under 35 U.S.C. 154(b) by 403 days.

(21) Appl. No.: 16/717,203

(22) Filed: Dec. 17, 2019

(65) Prior Publication Data

US 2020/0188365 A1   Jun. 18, 2020

Related U.S. Application Data

(60) Provisional application No. 62/780,382, filed on Dec. 17, 2018.

(51) Int. Cl.
*A61K 31/437* (2006.01)
*A61K 31/343* (2006.01)
*A61P 25/00* (2006.01)

(52) U.S. Cl.
CPC .......... *A61K 31/437* (2013.01); *A61K 31/343* (2013.01); *A61P 25/00* (2018.01)

(58) Field of Classification Search
CPC .............................. A61K 31/437; A61P 25/14
See application file for complete search history.

(56) References Cited

U.S. PATENT DOCUMENTS

| | | | |
|---|---|---|---|
| 4,278,676 A | 7/1981 | Krogsgaard-Larsenpovl |
| 4,353,910 A | 10/1982 | Perregaard |
| 4,362,731 A | 12/1982 | Hill |
| 5,929,065 A | 7/1999 | Lancel |
| 8,236,958 B2 | 8/2012 | Cooper |
| 8,569,355 B2 | 10/2013 | Laudon et al. |
| 9,339,495 B2 | 5/2016 | During |
| 9,351,968 B1 | 5/2016 | During |
| 9,399,034 B1 | 7/2016 | During et al. |
| 9,446,028 B2 | 9/2016 | During |
| 9,629,853 B2 | 4/2017 | Jones et al. |
| 9,682,069 B2 | 6/2017 | During |
| 9,717,716 B2 | 8/2017 | During et al. |
| 9,744,159 B2 | 8/2017 | During |
| 9,801,864 B2 | 10/2017 | During |
| 9,827,233 B1 | 11/2017 | During |
| 9,913,833 B2 | 3/2018 | During |
| 10,071,083 B2 | 9/2018 | During |
| 10,188,635 B2 | 1/2019 | During |
| 10,363,246 B1 | 7/2019 | During |
| 2002/0165217 A1 | 11/2002 | Howard |
| 2003/0077297 A1 | 4/2003 | Chen et al. |
| 2004/0024038 A1 | 2/2004 | Ebert et al. |
| 2005/0137222 A1 | 6/2005 | Ebert et al. |
| 2005/0164987 A1 | 7/2005 | Barberich |
| 2005/0215521 A1 | 9/2005 | Lalji et al. |
| 2005/0234093 A1 | 10/2005 | Sanchez et al. |
| 2007/0032553 A1 | 2/2007 | McKernan et al. |
| 2007/0112017 A1 | 5/2007 | Barlow et al. |
| 2008/0269278 A1 | 10/2008 | Lundahl et al. |
| 2009/0048288 A1 | 2/2009 | Ebert et al. |
| 2009/0143335 A1 | 6/2009 | Larsen et al. |
| 2009/0203731 A1 | 8/2009 | Sanchez et al. |
| 2009/0269795 A1 | 10/2009 | Smith |
| 2010/0093787 A1 | 4/2010 | Lundahl et al. |
| 2011/0046090 A1 | 2/2011 | Barlow et al. |
| 2012/0035207 A1 | 2/2012 | McKernan et al. |
| 2012/0302554 A1 | 11/2012 | Knipper-Breer et al. |
| 2013/0251671 A1 | 9/2013 | Kaufman et al. |
| 2015/0313913 A1 | 11/2015 | Catterall et al. |
| 2015/0352085 A1 | 12/2015 | During |
| 2017/0014393 A1 | 1/2017 | During |
| 2017/0042863 A1 | 2/2017 | During et al. |
| 2017/0065572 A1 | 3/2017 | During |
| 2017/0348232 A1 | 12/2017 | During |
| 2018/0042903 A1 | 2/2018 | During |
| 2018/0098974 A1 | 4/2018 | During |
| 2018/0140586 A1 | 5/2018 | During |
| 2018/0235942 A1 | 8/2018 | During et al. |
| 2018/0338960 A1 | 11/2018 | During |
| 2018/0344708 A1 | 12/2018 | During |
| 2019/0307733 A1 | 10/2019 | During |

FOREIGN PATENT DOCUMENTS

| | | |
|---|---|---|
| DE | 102005020882 A1 | 11/2006 |
| EP | 0000338 A2 | 1/1979 |
| EP | 0000338 A3 | 6/1979 |
| EP | 0840601 B1 | 10/2001 |
| EP | 1337247 B1 | 8/2006 |

(Continued)

OTHER PUBLICATIONS

Auger et al. J. Clin. Sleep Med., 2015, vol. 11, No. 10, pp. 1199-1236 (Year: 2015).*

Ebert et al., "Treating Insomnia: Current and Investigational Pharmacological Approaches," Pharmacology & Therapeutics, vol. 112, 2006; pp. 612-629.

Walsh et al.,, "The Selective Extrasynaptic GABA A Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.

James K. Walsh, Ph.D., "Enhancement of Slow Wave Sleep: Implications for Insomnia," Journal of Clinical Sleep Medicine, Supplement to vol. 5, No. 2, (2009); pp. 827-832.

International Search Report and Written Opinion of the International Searching Authority, dated Aug. 26, 2015, corresponding to International Application No. PCT/US15/34018; 12 total pages.

(Continued)

*Primary Examiner* — James D. Anderson
(74) *Attorney, Agent, or Firm* — Carter, DeLuca and Farrell LLP

(57) ABSTRACT

Treatment of non 24 sleep wake disorder using gaboxadol or a pharmaceutically acceptable salt thereof is provided. Pharmaceutical compositions that may be used to improve one or more symptoms of non 24 sleep wake disorder are provided.

11 Claims, 1 Drawing Sheet

(56) References Cited

FOREIGN PATENT DOCUMENTS

| | | |
|---|---|---|
| EP | 1641456 B1 | 3/2010 |
| JP | 2012501301 A | 1/2012 |
| WO | 97/02813 A1 | 1/1997 |
| WO | 2005023256 A1 | 3/2005 |
| WO | 2005058313 A1 | 6/2005 |
| WO | 2005094820 A1 | 10/2005 |
| WO | 2006013397 A1 | 2/2006 |
| WO | 2006118897 A1 | 11/2006 |
| WO | 2009021521 A2 | 2/2009 |
| WO | 2009056146 A1 | 5/2009 |
| WO | 2010015037 A1 | 2/2010 |
| WO | 2018144827 A1 | 8/2018 |

OTHER PUBLICATIONS

Deacon et al., "Effect of Short-Term Treatment with Gaboxadol on Sleep Maintenance and Initiation in Patients with Primary Insomnia," Sleep, vol. 30, No. 3, 2007; pp. 281-287.

Faulhaber et al., "The GABAA Agonist THIP Produces Slow Wave Sleep and Reduces Spindling Activity in NREM Sleep in Humans," Psychopharmacology, vol. 130, 1997; pp. 285-291.

Gaboxadol, from Wikipedia, the free encylopedia,http://en.wikipedia.org/wiki/Gaboxadol, 2014; 2 pages.

Gaboxadol, Investigational Agent—Drug Development Technology, http//www.drugdevelopment-technology.com/projects/gaboxadol—2014; 3 pages.

Gaboxadol, Bluelight, http://www.bluelight.org/vb/threads/370965-Gaboxadol—(2014); 1 page.

Glykys et al., "The Main Source of Ambident GABA Responsible for Tonic Inhibition in the Mouse Hippocampus," J Physiol, vol. 582, No. 3, 2007; pp. 1163-1178.

Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.

Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.

Jonas et al., "Neural Inhibition,", Scholarpedia—http://www.scholarpedia.org/article/Neural.sub.-inhibition-—(2014); 10 pages.

Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.

Marike Lancel, "Role of GABAA Receptors in the Regulation of Sleep: Initial Sleep Responses to Peripherally Administered Modulators and Agonists," Sleep, vol. 22, No. 1, (1999); pp. 33-42.

Lancel et al., "Effect of the GABAA Agonist Gaboxadol on Nocturnal Sleep and Hormone Secretion in Healthy Elderly Subjects," Am J. Physiol Endoctrinol Metab, vol. 281; (2001), pp. E130-E137.

Lundahl et al., "Short-term Treatment with Gaboxadol Improves Sleep Maintenance and Enhances Slow Wave Sleep in Adult Patients with Primary Insomnia," Psychopharmacology, vol. 195, (2007); pp. 139-146.

Mathias et al., "The GABAA Agonist Gaboxadol Improves the Quality of Post-Nap Sleep," Psychopharmacology, vol. 157 (2001); pp. 299-304.

Mathias et al., "Effect of Repeated Gaboxadol Administration on Night Sleep and Next-Day Performance in Healthy Elderly Subjects," Neuropsychopharmacology, vol. 30, (2005) pp. 833-841.

Natural Patterns of Sleep—Healthy Sleep—http://healthysleep.med.harvard.edu/healthy/science/what/sleep-pat-terns-rem-nrem (2007); 3 pages.

Olmos-Serrano et al, "The GABAA Receptor Agonist THIP Ameliorates Specific Behavioral Deficits in the Mouse Model of Fragile X Syndorme," Developmental Neuroscience, vol. 33, Fragile X Syndrome/Review, (2011), pp. 395-403.

International Search Report and Written Opinion of the International Searching Authority, dated Sep. 27, 2016, corresponding to International Application No. PCT/US16/42238; 8 total pages.

Egawa et al., "Pathophysiological power of improper tonic GABA(A) conductances in mature and immature models." Frontiers in Neural Circuits, Oct. 24, 2013, vol. 7, Article 170; pp. 1-15.

Peixoto et al., "Effects of gabaergic drugs on reserpine-induced oral dyskinesia," Behavioural Brain Research, vol. 160, (2005); pp. 51-59.

International Search Report and Written Opinion of the International Searching Authority, dated Aug. 14, 2015, corresponding to International Application No. PCT/US2015/029155; 19 total pages.

The United States Pharmacopeia (USP) disintegration test method set forth at section 701 Disintegration, Revision Bulletin Official Aug. 1, 2008; pp. 1-3.

Guidance for Industry, Orally Disintegrating Tablets, United States Department of Health and Human Services, Food and Drug Administration, Center for Drug Evaluation and Research (CDER), Dec. 2008, Chemistry, pp. 1-8.

Fu et al., "Drug Release Kinetics and Transport Mechanisms of Non-degradable and Degradable Polymeric Delivery Systems," NIH Public Access, Author Manuscript, National Institute of Health, Expert Opin Drug Deliv., Apr. 2010; vol. 7, No. 4 (pp. 429-444) 28 pages.

Boateng et al., "Characterisation of freeze-dried wafers and solvent evaporated films as potential drug delivery systems to mucosal surfaces," International Journal of Pharmaceutics, vol. 389, Issues 1-2, Apr. 15, 2010, pp. 24-31.

International Search Report and Written Opinion, dated Oct. 31, 2017, corresponding to International Applicaiton No. PCT/US17/46256; 10 total pages.

International Search Report and the Written Opinion of the International Searching Authority, dated Jul. 1, 2019, correpsonding to counterpart International Application No. PCT/US19/26218; 10 total pages.

International Search Report and Written Opinion of the International Searching Authority, dated Apr. 24, 2018, corresponding to International Application No. PCT/US218/16602; 15 total pages.

International Search Report and Written Opinion, dated Oct. 4, 2016, corresponding to International Application No. PCT/US16/50702; 9 total pages.

International Search Report and Written Opinion of the International Searching Authority, dated Jul. 18, 2017, corresponding to International Application No. PCT/US17/34443; 5 total pages.

Olmos-Serrano et al, "Defective GABAergic Neurotransmission and Pharmacological Rescue of Neuronal Hyperexcitability in the Amygdala in a Mouse Model of Fragile X Syndrome," The Journal of Neuroscience, vol. 30, No. 29, Jul. 21, 2010; pp. 9929-9938 (25 pages).

Iber et al., "The AASM Manual for the Scoring of Sleep and Associated Events," American Academy of Sleep Medicine (2007); pp. 3-59 (57 pages).

Braat et al., "The GABAA receptor is an FMRP target with therapeutic potential in fragile X syndrome," Cell Cycle (Sep. 15, 2015) vol. 14, No. 18; pp. 2985-2995.

Braat et al., "Insights into GABAAergic system deficits in fragile X syndrome lead to clinical trials," Neuropharmacology (Jan. 2015), vol. 88; pp. 48-54.

International Search Report and Written Opinion of the International Searching Authority, dated Apr. 24, 2018, corresponding to International Application No. PCT/US18/16602; 15 total pages.

International Search Report and Written Opinion of the International Searching Authority, dated Oct. 31, 2017, corresponding to International Patent Application No. PCT/US17/46256; 10 total pages.

European Search Report dated Nov. 18, 2019, corresponding to European Application No. 19190461.4; 11 pages.

Charles A. Handforth, "GABA Receptor May Present Target for New ET Drug Therapy," Essential Tremor, Jun. 4, 2013; 1 page.

Charles A. Handforth, "A Delta GABA Receptor as a Target for Essential Tremor Therapy," National Institutes of Health, Jun. 10, 2015; 4 pages.

International Search Report and Written Opinion, dated Jan. 27, 2020, corresponding to counterpart International Application No. PCT/US2019/059822; 8 total pages.

(56) References Cited

OTHER PUBLICATIONS

Krogsgaard-Larsen et al. "GABAA agonists and partial agonists: THIP (Gaboxadol) as a non-opioid analgesic and a novel type of hypnotic," Biochemical Pharmacology 2004 (68) 1573-1580 (Year: 2004).
Walter Alexander, "Sleep: Gaboxadol Enhances Slow Wave Sleep," Perelman, School of Medicine, Jun. 22, 2006; 3 pages.
Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.
Larsen et al.,—Research Paper—"Intestinal Gaboxadol Absorption via PAT1 (SLC36A1): Modified Absorption in vivo Following Co-administration of L-tryptophan," British Journal of Pharmacology (BJP), vol. 157, (2009); pp. 1380-1389.
Vardya et al., "Positive Modulation of .delta.-Subunit Containing GABAA Receptors in Mouse neurons" Neuropharmacology, vol. 63; 2012; pp. 469-479.
Brawn et al., "Circadian Rhythm Sleep Disorder, Free-Running Type in a Sighted Male with Severe Depression, Anxiety, and Agoraphobia," Journal of Clinical Sleep Medicine, vol. 7, No. 1, (2011); pp. 93-94.
Abbott, "Non-24-hour Sleep-Wake Rhythm Disorder," Neurologic Clinics, vol. 37, Issue 3, Aug. 2019; p. 545.
International Search Report and Written Opinion of the International Searching Authority, dated Apr. 1, 2020, corresponding to counterpart International Application No. PCT/US19/66817; 7 total pages.
Curia et al., "Downregulation of Tonic GABAergic Inhibition in a Mouse Model of Fragile X Syndrome," Cerebral Cortex (Jul. 2009), vol. 19; pp. 1515-1520.
Gantois et al., Expression profiling suggests underexpression of the GABA(A) receptor subunit delta in the fragile X knockout mouse model, ' Neurobiol Dis (2006), vol. 21, No. 2; pp. 346-357.
PCT Notice concerning Transmittal of International Preliminary Report on Patentability (Chapter I of the Patent Cooperation Treaty) dated Feb. 1, 2018; International Preliminary Report on Patentability dated Jan. 23, 2018; and Written Opinion of the International Searching Authority, dated Sep. 27, 2016, corresponding to International Application No. PCT/US2016/042238; 8 total pages.
Reagan-Shaw et al., "Dose translation from animal to human studies revisited", FASEB J, vol. 22, No. 3, Oct. 17, 2007; pp. 659-661.
Oakley et al., "Synergistic GABA-Enhancing Therapy against Seizures in a Mouse Model of Dravet Syndrome," The Journal of Pharmacology and Experimental Therapeutics, vol. 345, May 2013; pp. 215-224.
Nagar et al., "Orally disintegrating tablest: formulation, preparation techniques and evaluation", Journal of Applied Phramaceutical Science, vol. 01, No. 04, 2011; pp. 35-45.
Gupta Nitan Bharti et al., "Pulsatile Drug Delivery as Modified Release Dosage Form: A Review", Journal of Drug Delivery & Therapeutics, vVI. 2, No. 6, 2012; pp. 102-110.
Reddy et al., "Review On: Pulsatile Drug Delivery Systems", Journal of Pharmacetucial Sciences and Research, (ISSN: 0975-1459), vol. 1, No. 4, 2009; pp. 109-115.
Bharawaj et al., "Orally Disintegrating Tablets: A Review", Drug Invention Today, vol. 2, No. 1, (ISSN: 0975-7619), 2010; pp. 81-88.
Boyle et al., "Tolerability, pharmacokinetics and night-time effects on postural sway and critical flicker fusion of gaboxadol and zolpidem in elderly subjects," British Journal of Clinical Pharmacology, 2008, vol. 67, No. 2; pp. 180-190.
Yapar et al., "Orally Disintegrating Tablets: An Overview," Journal of Applied Pharmaceutical Science, Feb. 2014, vol. 4, No. 02, pp. 118-125.
Kesisoglou et al., "Utility of PBPK Absorption Modeling to Guide Modified Release Formulation Development of Gaboxadol, a Highly Soluble Compound with Region-Dependent Absorption," Research Article—Pharmaceutics, Drug Delivery and PharmaceuticalTechnology, Aug. 19, 2015; Journal of Pharmacetuical Sciences, vol. 105; pp. 722-728 (7 pages).
Boyle et al., "Next-day residual effects of gaboxadol and flurazepam administered at bedtime: a randomized double-blind study in healthy elderly subjects," Human Psychopharmacology, 2009, vol. 24, pp. 61-71.
Chaturvedi et al., "Fast Dissolving Films: A Review," Current Drug Delivery, 2011, vol. 8; pp. 373-380.
Ciper and Bodmeier, "Preparation and characterization of novel fast disintegrating capsules (Fastcaps) for administration in the oral cavity," Science Direct, International Journal of Pharmaceutics, 2005, vol. 303; pp. 62-71.
Journal of Labelled Compounds and Radiopharmaceuticals, "Deuterium Labelling of the Gaba Agonists THIP, Piperidine-4-Sulphonic Acid and the Gaba Uptake Inhibitor THPO," (1982), vol. XIX, No. 5; pp. 689-702.
Cheng et al., "Inducing Anesthesia with a GABA Analog, THIP,", Anesthesiology, vol. 63, No. 2, Aug. 1985; pp. 147-151.
Ransdell Pierson, Update 2-Merck, Lundbeck scrap insomnia drug after trials, Rueters, (Dow Jones); Mar. 26, 2007; 2 pages.
Stephanie Saul, "Merck Cancels Work on a New Insomnia Medication," The New York Times, Mar. 29, 2007; 2 pages.
Loescher, W., "Development of Tolerance to the Anticonvulsant Effect of GABA-mimetic Drugs in Animal Models of Seizure States in Tolerance to Beneficial and Adverse Effects of Antiepileptic Drugs," (1986), Koella et al. (eds.), pp. 37-45.
Petersen et al., "THIP: A Single Blind Controlled Trial in Patients with Epilepsy," Acta Neurol. Scand. 67; (1983) pp. 114-117.
Albers, H. Elliot, et al., "The dynamics of GABA signaling: revelations from the circadian pacemaker in the suprachiasmatic nucleus," Frontiers in neuroendocrinology, Jan. 2017, pp. 35-82, 44.
European Supplemental Search Report for related application No. 19901141.2, dated Jun. 29, 2022, 7 pages.

\* cited by examiner

USE OF GABOXADOL FOR THE TREATMENT OF NON-24 HOUR SLEEP-WAKE DISORDER

CROSS-REFERENCE TO RELATED APPLICATION

This application claims benefit and priority to U.S. Provisional Application No. 62/780,382, filed Dec. 17, 2018, which is incorporated herein by reference in its entirety.

TECHNICAL FIELD

Treatment of non-24 hour sleep-wake disorder.

BACKGROUND

Non-24-hour sleep wake disorder (Non-24) is a disorder that affects the normal 24-hour synchronization of circadian rhythms. Non-24-hour sleep wake disorder is also known as hypernychthemeral syndrome. People with non 24 hour sleep wake disorder have circadian rhythms that are not synchronized with the 24-hour day-night cycle. According to the National Institutes of Health, Genetic and Rare Diseases Information Center, non 24 hour sleep wake disorder refers to a steady pattern of one- to two-hour delays in sleep onset and wake times in people with normal living conditions. This occurs because the period of the person's sleep-wake cycle is longer than 24 hours. The condition most commonly affects people who are blind, due to an impaired sense of light-dark cycles. However, non 24 hour sleep wake disorder can also affect sighted people. Non 24 hour sleep wake disorder can be disruptive to normal functioning. For example, people with this disorder may find it difficult to follow a regular schedule, since their biological clock can shift to make them sleepy during the day and experience insomnia during night. Treatment of non-24 sleep wake disorder can involve administration of melatonin before bedtime. The US Food and Drug Administration (FDA) has approved a melatonin agonist, tasimelteon, for the treatment of non-24 sleep wake disorder for blind people. Light therapy is also utilized to treat non-24 sleep wake disorder.

Gaboxadol (4,5,6,7-tetrahydroisoxazolo [5,4-c]pyridine-3-ol) (THIP)) is described in EP Patent No. 0000338 and in EP Patent No. 0840601, U.S. Pat. Nos. 4,278,676, 4,362,731, 4,353,910, and WO 2005/094820. Gaboxadol is a selective $GABA_A$ receptor agonist with a preference for δ-subunit containing $GABA_A$ receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia. The development was discontinued after the compound failed to show significant effects in sleep onset and sleep maintenance in a three-month efficacy study. Additionally, patients with a history of drug abuse who received gaboxadol experienced a steep increase in psychiatric adverse events.

SUMMARY

Methods of treating non-24 sleep wake disorder are provided which include administering to a patient in need thereof gaboxadol or a pharmaceutically acceptable salt thereof. Methods of treating non-24 sleep wake disorder include administering gaboxadol or a pharmaceutically acceptable salt thereof to a patient in need thereof to provide improvement in one or more symptoms of the non-24 sleep wake disorder. Methods of treating non-24 sleep wake disorder described herein also include administering to a patient in need thereof gaboxadol or a pharmaceutically acceptable salt thereof wherein the method provides improvement in next day functioning of the patient. Methods of treating non-24 sleep wake disorder described herein also include administering to a patient in need thereof gaboxadol or a pharmaceutically acceptable salt thereof wherein the method provides improvement in the patient for more than 4, 6, 8, 10, 12, 14, 16, 18, 20, 22, or 24 or more hours after administration to the patient. Methods of treating non-24 sleep wake disorder described herein also include administering to a patient in need thereof gaboxadol or a pharmaceutically acceptable salt thereof wherein the method provides improvement in the patient for at least 4, 6, 8, 10, 12, 14, 16, 18, 20, 22, or 24 or more hours after administration to the patient. Pharmaceutical compositions including gaboxadol or a pharmaceutically acceptable salt thereof are provided for use in treating non-24 sleep wake disorder. Methods of treating non-24 sleep wake disorder include administering a pharmaceutical composition including gaboxadol or a pharmaceutically acceptable salt thereof to a patient in need thereof. In embodiments, methods of treating non-24 sleep wake disorder include administering gaboxadol or a pharmaceutically acceptable salt thereof to a patient in need thereof to provide improvement in symptoms of the non-24 sleep wake disorder in the patient a day after administration of the gaboxadol or a pharmaceutically acceptable salt thereof.

Methods of treating non-24 sleep wake disorder described herein include administering to a patient in need thereof about 0.05 mg to about 30 mg gaboxadol or a pharmaceutically acceptable salt thereof wherein the method provides improvement in non-24 sleep wake disorder. Methods of treating non-24 sleep wake disorder described herein include administering to a patient in need thereof a composition including about 0.05 mg to about 30 mg gaboxadol or a pharmaceutically acceptable salt thereof wherein the composition provides improvement in non-24 sleep wake disorder. Methods of treating non-24 sleep wake disorder described herein include administering to a patient in need thereof about 0.05 mg to about 30 mg gaboxadol or a pharmaceutically acceptable salt thereof wherein the method provides improvement in one or more symptoms of non-24 sleep wake disorder. Methods of treating non-24 sleep wake disorder described herein include administering to a patient in need thereof a composition including about 0.05 mg to about 30 mg gaboxadol or a pharmaceutically acceptable salt thereof wherein the composition provides improvement in one or more symptoms of non-24 sleep wake disorder. Methods of treating non-24 sleep wake disorder described herein include administering to a patient in need thereof about 0.05 mg to about 30 mg gaboxadol or a pharmaceutically acceptable salt thereof wherein the method provides improvement in non-24 sleep wake disorder the next day. Methods of treating non-24 sleep wake disorder described herein include administering to a patient in need thereof a composition including about 0.05 mg to about 30 mg gaboxadol or a pharmaceutically acceptable salt thereof wherein the composition provides improvement in non-24 sleep wake disorder the next day. Methods of treating non-24 sleep wake disorder described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating non-24 sleep wake disorder described herein include administering to a patient in need thereof a composition including about 0.05 mg to about 30 mg gaboxadol or a pharmaceutically acceptable salt thereof wherein the composition provides improvement in the patient for more than 6 hours after administration to the patient. Methods of treating non-24 sleep wake disorder are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating non-24 sleep wake disorder are described herein which include administering to a patient in need thereof a composition including gaboxadol or a pharmaceutically acceptable salt thereof wherein the composition provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating non-24 sleep wake disorder are described herein which include administering to a patient in need thereof gaboxadol or a pharmaceutically acceptable salt thereof wherein the method provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating non-24 sleep wake disorder are described herein which include administering to a patient in need thereof a composition including gaboxadol or a pharmaceutically acceptable salt thereof wherein the composition provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating non-24 sleep wake disorder are described herein which include administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least 20% less than the first pharmaceutical composition. Methods of treating non-24 sleep wake disorder are described herein which include administering to a patient in need thereof about 0.05 mg to about 30 mg gaboxadol or a pharmaceutically acceptable salt thereof in combination with melatonin or a melatonin agonist wherein the method provides improvement in non-24 sleep wake disorder.

DETAILED DESCRIPTION

Figure 1:
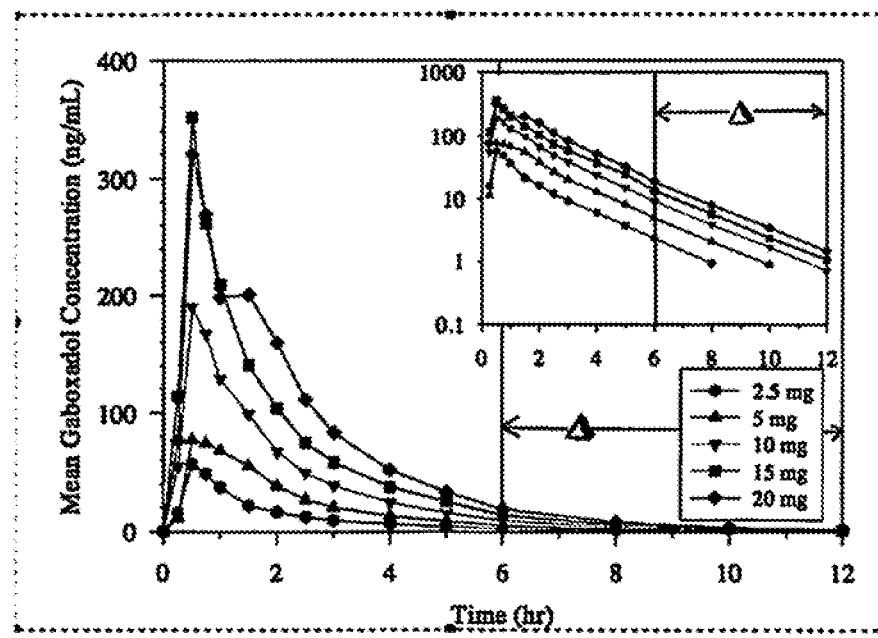
FIG. 1 shows the arithmetic mean plasma concentration-time profiles of gaboxadol following single oral doses (2.5, 5, 10, 15, and 20 mg) as described in Example 1 with horizontal lines Δ indicating the change between 6 and 12 hours.

Described herein are methods of treating non-24 sleep wake disorder (Non-24) with gaboxadol or a pharmaceutically acceptable salt thereof. Methods of treating non-24 sleep wake disorder described herein include administering to a patient in need thereof gaboxadol or a pharmaceutically acceptable salt thereof wherein the method provides improvement in one or more symptoms of non-24 sleep wake disorder. Methods of treating non-24 sleep wake disorder described herein also include administering to a patient in need thereof gaboxadol or a pharmaceutically acceptable salt thereof wherein the method provides improvement in next day functioning of the patient. Methods of treating non-24 sleep wake disorder described herein also include administering to a patient in need thereof gaboxadol or a pharmaceutically acceptable salt thereof wherein the method provides improvement in the patient for more than 4, 6, 8, 10, 12, 14, 16, 18, 20, 22, or 24 or more hours after administration of gaboxadol or a pharmaceutically acceptable salt thereof to the patient. Methods of treating non-24 sleep wake disorder described herein also include administering to a patient in need thereof gaboxadol or a pharmaceutically acceptable salt thereof wherein the method provides improvement in the patient for at least 4, 6, 8, 10, 12, 14, 16, 18, 20, 22, or 24 or more hours after administration of gaboxadol or a pharmaceutically acceptable salt thereof to the patient.

Symptoms of non 24 sleep wake disorder include irregular sleep patterns, irregular circadian rhythms, insomnia, apraxia including ideational apraxia, ideomotor apraxia, kinetic apraxia, limb apraxia, verbal apraxia, cognitive dysfunction, difficulties concentrating, confusion, depressed mood, diarrhea, nausea, fatigue, hair loss, headache, impaired balance, photosensitivity, joint pain, loss of muscle coordination (ataxia), menstrual irregularities, muscle pain, suicidal thoughts, weight gain, and hallucinations.

Many pharmaceutical products are administered as a fixed dose, at regular intervals, to achieve therapeutic efficacy. A drug's duration of action is reflected by its plasma half-life. Gaboxadol is a selective $GABA_A$ receptor agonist with a relatively short half-life (t½=1.5 h). Since efficacy is often dependent on sufficient exposure within the central nervous system administration of CNS drugs with a short half-life may require frequent maintenance dosing.

Advantageously disclosed herein are methods of treating non 24 sleep wake disorder by administration of gaboxadol or a pharmaceutically acceptable salt thereof. In embodiments, methods of treating non 24 sleep wake disorder are provided which include administering to a patient in need thereof a pharmaceutical composition including about 0.05 mg to about 30 mg gaboxadol or a pharmaceutically acceptable salt thereof wherein the composition provides improvement for at least 4 hours after administration to the patient. In embodiments, methods of treating non 24 sleep wake disorder are provided which include administering to a patient in need thereof a pharmaceutical composition including about 0.05 mg to about 30 mg gaboxadol or a pharmaceutically acceptable salt thereof wherein the composition provides improvement for at least 6 hours after administration to the patient. In embodiments, methods of treating non 24 sleep wake disorder are provided which include administering to a patient in need thereof a pharmaceutical composition including about 0.05 mg to about 30 mg gaboxadol or a pharmaceutically acceptable salt thereof wherein the composition provides improvement for more than 6 hours after administration to the patient.

Methods of treating non 24 sleep wake disorder described herein include administering to a patient in need thereof about 0.05 mg to about 30 mg gaboxadol or a pharmaceutically acceptable salt thereof wherein the method provides improvement in one or more symptoms of non 24 sleep wake disorder. Methods of treating non 24 sleep wake disorder described herein include administering to a patient in need thereof about 0.05 mg to about 30 mg gaboxadol or a pharmaceutically acceptable salt thereof wherein the method provides improvement in non 24 sleep wake disorder the next day after administration. Methods of treating non 24 sleep wake disorder described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating non 24 sleep wake disorder are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating non 24 sleep wake disorder are described herein which include administering to a patient in need thereof gaboxadol or a pharmaceutically acceptable salt thereof wherein the method provides an in vivo plasma profile comprising a $AUC_{6-12}$ of less than about 900 ng ng·hr/ml and wherein the method provides improvement in the patient for more than 6 hours after administration of the gaboxadol or a pharmaceutically acceptable salt thereof. Methods of treating non 24 sleep wake disorder are described herein which include administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

Embodiments described herein provide that a patient in need thereof is administered a pharmaceutical composition including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylene-salicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about 0.0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, methods of treating non 24 sleep wake disorder include administering to a patient in need thereof a pharmaceutical composition including about 0.05 mg to about 30 mg gaboxadol or a pharmaceutically acceptable salt thereof.

In embodiments, the pharmaceutical compositions include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions include 0.1 mg, 0.25 mg, 0.5 mg, 1 mg, 2.5 mg, 3 mg, 4 mg, 5 mg, 7 mg, 7.5 mg, 8 mg, 8.5 mg, 9 mg, 9.5 mg, 10 mg, 10.5 mg, 11 mg, 12 mg, 12.5 mg, 13 mg, 14 mg, 15 mg, 16 mg, 17 mg, 17.5 mg, 18 mg, 19 mg, 20 mg, 21 mg, 22 mg, 23 mg, 24 mg, 25 mg, 26 mg, 27 mg, 28 mg, 29 mg, or 30 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

In embodiments, pharmaceutical compositions herein may be provided in the form of tablets, capsules, suppositories, inhalants, solutions, suspensions or emulsions. Pharmaceutical compositions (also referred to herein as "pharmaceutical formulations" or simply "formulations") herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. In embodiments, pharmaceutical compositions herein are suitable for parenteral administration, including, e.g., intramuscularly (i.m.), intravenously (i.v.), subcutaneously (s.c.), intraperitoneally (i.p.), or intrathecally (i.t.). The parenteral compositions herein must be sterile for administration by injection, infusion or implantation into the body and may be packaged in either single-dose or multi-dose containers. The parenteral compositions may be contained in a bag, a glass vial, a plastic vial, or a bottle.

In embodiments, liquid pharmaceutical compositions for parenteral administration to a subject including gaboxadol or a pharmaceutically acceptable salt thereof at a concentration of about 0.005 µg/ml to about 500 µg/ml are provided. In embodiments, the composition includes gaboxadol or a pharmaceutically acceptable salt thereof at a concentration of, e.g., about 0.005 µg/ml to about 250 µg/ml, about 0.005 µg/ml to about 200 µg/ml, about 0.005 µg/ml to about 150 µg/ml, about 0.005 µg/ml to about 100 µg/ml, or about 0.005 µg/ml to about 50 µg/ml.

In embodiments, compositions for parenteral administration include gaboxadol or a pharmaceutically acceptable salt thereof at a concentration of, e.g., about 0.05 µg/ml to about 50 µg/ml, about 0.1 µg/ml to about 50 µg/ml, about 0.05 µg/ml to about 25 µg/ml, about 0.05 µg/ml to about 10 µg/ml, about 0.05 µg/ml to about 5 µg/ml, or about 0.05 µg/ml to about 1 µg/ml. In embodiments, a composition for parenteral administration includes gaboxadol or a pharmaceutically acceptable salt thereof at a concentration of, e.g., about 0.05 µg/ml to about 15 µg/ml, about 0.5 µg/ml to about 10 µg/ml, about 0.5 µg/ml to about 7 µg/ml, about 1 µg/ml to about 10 µg/ml, about 5 µg/ml to about 10 µg/ml, or about 5 µg/ml to about 15 µg/ml. In embodiments, pharmaceutical compositions for parenteral administration are formulated as a total volume of about, e.g., 10 ml, 20 ml, 25 ml, 50 ml, 100 ml, 200 ml, 250 ml, or 500 ml.

In embodiments, compositions for parenteral administration including about 0.05 mg to about 100 mg gaboxadol or a pharmaceutically acceptable salt thereof are provided. In embodiments, the pharmaceutical compositions include about, e.g., 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions for parenteral administration include about, e.g., 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof. In embodiments, the pharmaceutical compositions for parenteral administration include about, e.g., 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses.

In embodiments, pharmaceutical compositions for parenteral administration including gaboxadol or a pharmaceutically acceptable salt thereof wherein the gaboxadol or pharmaceutically acceptable salt thereof is present at a molarity less than about 1.0 M are provided. In embodiments, gaboxadol or pharmaceutically acceptable salt thereof is present at a molarity greater than, e.g., about 0.0001 M about 0.001 M, about 0.01 M, about 0.1 M, about 0.2 M, greater than about 0.5, greater than about 1.0 M, greater than about 1.2 M, greater than about 1.5 M, greater than about 1.75 M, greater than about 2.0 M, or greater than about 2.5 M. In embodiments, gaboxadol or pharmaceutically acceptable salt thereof is present at a molarity of between, e.g., about 0.00001 M to about 0.1 M, about 0.01 to about 0.1 M, about 0.1 M to about 1.0 M, about 1.0 M to about 5.0 M, or about 5.0 M to about 10.0 M. In embodiments, gaboxadol or pharmaceutically acceptable salt thereof is present at a molarity of less than, e.g., about 0.01 M, about 0.1 M, about 1.0 M, about 5.0 M, or about 10.0 M In embodiments, the solubility of gaboxadol or pharmaceutically acceptable salt thereof in the composition for parenteral administration is greater than, e.g., about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 150 mg/mL, when measured, for example, in water at 25° C.

In embodiments, the solubility of gaboxadol or pharmaceutically acceptable salt thereof in the composition for parenteral administration is between, e.g., about 1 mg/mL to about 50 mg/mL, about 5 mg/mL to about 50 mg/mL, about 10 mg/mL to about 50 mg/mL, about 20 mg/mL to about 50 mg/ml, from about 20 mg/mL to about 30 mg/mL or from about 10 mg/mL to about 45 mg/mL, when measured, for example, in water at 25 C.

In embodiments, a pharmaceutical composition for parenteral administration is provided wherein the pharmaceutical composition is stable for at least six months. In embodiments, the pharmaceutical compositions herein exhibit no more than about 5% decrease in gaboxadol or pharmaceutically acceptable salt thereof after, e.g., 3 months or 6 months. In embodiments, the amount of gaboxadol or pharmaceutically acceptable salt thereof degradation is no more than about, e.g., 2.5%, 1%, 0.5% or 0.1%. In embodiments, the degradation of gaboxadol or pharmaceutically acceptable salt thereof is less than about, e.g., 5%, 2.5%, 1%, 0.5%, 0.25%, 0.1%, for at least six months.

In embodiments, pharmaceutical compositions for parenteral administration wherein the pharmaceutical composition remains soluble are provided. In embodiments, pharmaceutical compositions that are stable, soluble, local site compatible and/or ready-to-use are provided. In embodiments, the pharmaceutical compositions herein are ready-to-use for direct administration to a patient in need thereof.

The parenteral compositions herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of gaboxadol or pharmaceutically acceptable salt used in the composition. Thus, parenteral compositions are provided wherein there is no incompatibility between any of the components of the dosage form.

Thus, in embodiments, parenteral compositions of gaboxadol or a pharmaceutically acceptable salt thereof including a stabilizing amount of at least one excipient are provided. For example, excipients may be selected buffering agents, solubilizing agents, tonicity agents, antioxidants, chelating agents, antimicrobial agents, preservatives, and combinations thereof. One skilled in the art will appreciate that an excipient may have more than one function and be classified in one or more defined group.

In embodiments, pharmaceutical compositions for parenteral administration are provided including gaboxadol, or a pharmaceutically acceptable salt thereof and an excipient wherein the excipient comprises a stabilizing amount of a buffering agent. In embodiments, the buffering agent can be a citrate, phosphate, acetate, tartrate, carbonate, glutamate, lactate, succinate, bicarbonate buffer and combinations thereof. For example, sodium citrate, trisodium citrate anhydrous, trisodium citrate dihydrate, sodium citrate dehydrate, triethanolamine (TRIS), trisodium citrate pentahydrate dihydrate (i.e., trisodium citrate dehydrate), acetic acid, citric acid, glutamic acid, phosphoric acid, may be used as a buffering agent. In embodiments, the buffering agent may be an amino acid, alkali metal, or alkaline earth metal buffer. For example, the buffering agent may be sodium acetate or hydrogen phosphate. In embodiments, provided herein are parenteral compositions of gaboxadol of pharmaceutically acceptable salts thereof wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution of gaboxadol is, e.g., about 6.8, about 7.0, about 7.2, about 7.4, about 7.6, about 7.7, about 7.8, about 8.0, about 8.2, about 8.4, or about 8.6.

In embodiments, pharmaceutical compositions for parenteral administration are provided including gaboxadol, or a pharmaceutically acceptable salt thereof and an excipient wherein the excipient includes a solubilizing agent. For example, solubilizing agents according to the invention may include, e.g., sodium hydroxide, L-lysine, L-arginine, sodium carbonate, potassium carbonate, sodium phosphate, and/or potassium phosphate. In embodiments, provided herein are pharmaceutical compositions including gaboxadol, or a pharmaceutically acceptable salt thereof and an excipient wherein the excipient includes a particulate formation inhibitor. A particulate formation inhibitor refers to a compound that has the desired property of inhibiting the formation of particles in parenteral compositions. Particulate formation inhibitors of the invention include ethylenediaminetetraacetic acid (EDTA) and salts thereof, for example, ethylenediaminetetraacetic acid, calcium disodium salt (preferably as the hydrate); ethylenediaminetetraacetic acid, diammonium salt (preferably as the hydrate); ethylenediaminetetraacetic acid, dipotassium salt (preferably as the dihydrate); ethylenediaminetetraacetic acid, disodium salt (preferably as the dihydrate and, if desired, as the anhydrous form); ethylenediaminetetraacetic acid, tetrasodium salt (preferably as the hydrate); ethylenediaminetetraacetic acid, tripotassium salt (preferably as the dihydrate); ethylenediaminetetraacetic acid, trisodium salt (preferably as the hydrate) and ethylenediaminetetraacetic acid disodium salt, USP (preferably as the dihydrate).

In embodiments, provided herein are pharmaceutical compositions for parenteral administration including gaboxadol or a pharmaceutically acceptable salt thereof and an excipient wherein the excipient includes a solubilizing agent. For example, solubilizing agents may include, but are not limited to, acids, such as carboxylic acids, amino acids. In other examples, the solubilizing agents may be saturated carboxylic acids, unsaturated carboxylic acids, fatty acids, keto acids, aromatic carboxylic acids, dicarboxylic acids, tricarboxylic acids, α-hydroxy acids, amino acids, formic acid, acetic acid, propionic acid, butyric acid, valeric acid, caproic acid, enanthic acid, caprylic acid, pelargonic acid, capric acid, lauric acid, stearic acid, acrylic acid, docosahexaenoic acid, eicosapentaenoic acid, pyruvic acid, benzoic acid, salicylic acid, aldaric acid, oxalic acid, malonic acid, malic acid, succinic acid, glutaric acid, adipic acid, citric acid, lactic acid, alanine, arginine, aspargine, aspartic acid, cysteine, glutamine, glycine, histidine, isoleucine, leucine, lysine, methionine, phenylalanine, praline, serine, threonine, tryptophan, tyrosine, valine, and combinations thereof.

In embodiments, provided herein are pharmaceutical compositions for parenteral administration including gaboxadol or a pharmaceutically acceptable salt thereof and an excipient wherein the excipient renders the composition isotonic. Isotonic pharmaceutical compositions herein may be achieved by adding an appropriate quantity of sodium chloride, glucose, laevulose, dextrose, mannitol, or potassium chloride, or calcium chloride, or calcium gluconoglucoheptonate, or mixtures thereof. In embodiments, provided herein are pharmaceutical compositions including gaboxadol, or a pharmaceutically acceptable salt thereof and an excipient wherein the excipient includes a free radical antagonist. In embodiments, the free radical antagonist is ascorbic acid, ascorbic acid derivatives, organic compounds having at least one thiol, alkyl polyhydroxylated, and cycloalkyl polyhydroxylated compounds, and combinations thereof.

In embodiments, provided herein are pharmaceutical compositions for parenteral administration including gaboxadol, or a pharmaceutically acceptable salt thereof and an excipient wherein the excipient includes a preservative. In embodiments, the preservative is selected from benzalkonium chloride, benzethonium chloride, benzyl alcohol, chlorobutanol, chlorocresol, metacresol, Phenol, phenylmercuric nitrate, phenylmercuric acetate, methyl p-hydroxybenzoate, propyl p-hydroxybenzoate, butyl p-hydroxybenzoate, and thimerosal. In other embodiments, the preservative is selected from the group consisting of phenol, meta-cresol, benzyl alcohol, parabens (e.g., methyl, propyl, butyl), benzalkonium chloride, chlorobutanol, thimerosal, phenylmercuric salts (e.g., acetate, borate, or nitrate), and combinations thereof.

When administered, the parenteral compositions herein provide a time of maximum plasma concentration ($T_{max}$) for gaboxadol in human patients of about 1 or more hours (e.g., about 1.5 or more hours). In embodiments, a $T_{max}$ of gaboxadol in human patients ranging from between, e.g., about 1 to about 5 hours, about 1 to about 4 hours, about 1 to about 3 hours, about 1 to about 2 hours. In embodiments, a $T_{max}$ for gaboxadol in human patients of more than about 1.5 is observed. In embodiments, a $T_{max}$ for gaboxadol in human patients of less than about 3 hours is observed. The time of maximum plasma concentration is measured once infusion is complete.

In embodiments herein a dosage form includes from about 1 mg to about 500 mg gaboxadol, wherein parenteral administration (e.g., intramuscular, intravenous, subcutaneous, intraperitoneal, or intrathecal) of the dosage form provides an in vivo plasma profile for gaboxadol comprising a mean $AUC_{0-\infty}$ of more than about 25 ng·hr/ml. In embodiments, single dose administration of the dosage form provides an in vivo plasma profile for gaboxadol comprising a mean $AUC_{0-\infty}$ of more than about, e.g., 50 ng·hr/ml, 75 ng·hr/ml, 150 ng·hr/ml, 250 ng·hr/ml, 500 ng·hr/ml, 1000 ng·hr/ml, or 1500 ng·hr/ml.

In embodiments, the dosage form for parenteral administration includes from about 1 mg to about 500 mg gaboxadol, wherein administration of the dosage form provides an in vivo plasma profile for gaboxadol comprising a mean $C_{max}$ of less than about 10000 ng/ml. In embodiments, single dose administration of the compositions for parenteral administration provide an in vivo plasma profile for gaboxadol of a mean $C_{max}$ of less than about, e.g., 5000 ng/ml, 2500 ng/ml, 1000 ng/ml, 500 ng/ml, 250 ng/ml, or 100 ng/ml.

In embodiments, pharmaceutical compositions for parenteral administration include gaboxadol or a pharmaceutically acceptable salt thereof wherein parenteral administration exhibits a pharmacokinetic profile of a $T_{max}$ at about 1 to about 120 minutes after administration of the parenteral composition; followed by a plasma drug concentration of at least 50% $C_{max}$ for a duration of about 90 to about 360 minutes. In embodiments, parenteral administration of gaboxadol is followed by a plasma drug concentration of at least 50% $C_{max}$ for a duration of, e.g., about 10 to about 60 minutes, about 15 to about 90 minutes, about 30 to about 120 minutes, about 60 to about 180 minutes, about 90 to about 180 minutes.

As mentioned previously pharmaceutical compositions herein may be conventional or modified, i.e., provided with conventional release profiles or modified release profiles. Conventional (or unmodified) release oral dosage forms such as tablets or capsules typically release medications into the stomach or intestines as the tablet or capsule shell dissolves. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. In embodiments, when administered to an oral cavity, an ODDF herein disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds.

An orally disintegrating tablet (ODT) is a solid dosage form containing a medicinal substance or active ingredient which disintegrates rapidly, usually within a matter of seconds when placed upon the tongue. The disintegration time for ODTs generally ranges from several seconds to about a minute. ODTs are designed to disintegrate or dissolve rapidly on contact with saliva, thus eliminating the need to chew the tablet, swallow the intact tablet, or take the tablet with liquids. In embodiments, an ODT herein disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds, based upon, e.g., the United States Pharmacopeia (USP) disintegration test method set forth at section 701, Revision Bulletin Official Aug. 1, 2008.

Other ODDFs which may be used herein include rapidly dissolving films which are thin oral strips that release medication such as gaboxadol or a pharmaceutically acceptable salt thereof quickly after administration to the oral cavity. The film is placed on a patient's tongue or any other mucosal surface and is instantly wet by saliva whereupon the film rapidly hydrates and dissolves to release the medication. See. e.g., Chaturvedi et al., *Curr Drug Deliv.* 2011 July; 8(4):373-80. Fastcaps are a rapidly disintegrating drug delivery system based on gelatin capsules. Freeze dried (lyophilized) wafers are rapidly disintegrating, thin matrixes that contain a medicinal agent. The wafer or film disintegrates rapidly in the oral cavity and releases drug which dissolves or disperses in the saliva. See, e.g., Boateng et al., *Int J Pharm.* 2010 Apr. 15; 389(1-2):24-31. Those skilled in the art are familiar with various techniques utilized to manufacture ODDFs such as freeze drying, spray drying, phase transition processing, melt granulation, sublimation, mass extrusion, cotton candy processing, direct compression, etc.

When administered, ODDFs containing gaboxadol or a pharmaceutically acceptable salt thereof, either alone or in combination with one or more additional drugs discussed herein, e.g., melatonin or tasimelteon (collectively referred to herein as "drug", "drugs", "active agent", or "active agents"), disintegrate rapidly to release the drug(s), which dissolves or disperses in the saliva. The drug may be absorbed in the oral cavity, e.g., sublingually, buccally, from the pharynx and esophagus or from other sections of gastrointestinal tract as the saliva travels down. In such cases, bioavailability can be significantly greater than that observed from conventional tablet dosage forms which travel to the stomach or intestines where drug can be released.

In embodiments, pharmaceutical compositions having modified release profiles provide pharmacokinetic properties which result in both rapid onset and sustained duration of action. Such pharmaceutical compositions can include an immediate release aspect and an extended release aspect. Immediate release aspects are discussed above in connection with ODDFs. Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. In embodiments, modified release dosage forms herein can be ERDFs that do not have an ODDF aspect. In embodiments, modified release dosage forms herein incorporate an ODDF aspect to provide immediate release of a loading dose and then an ERDF aspect that provides prolonged delivery to maintain drug levels in the blood within a desired therapeutic range for a desirable period of time in excess of the activity resulting from a single dose of the drug. In embodiments, the ODDF aspect releases the drug immediately and the ERDF aspect thereafter provides continuous release of drug for sustained action.

In embodiments, an ODDF can be applied as a coating or band over an ERDF, or as a layer adjacent to an ERDF, to allow direct exposure of the ODDF to the oral cavity and consequent disintegration of the ODDF. In embodiments, the ODDF and the ERDF can be mixed in a chewable resin, e.g., gum. Those skilled in the art are familiar with techniques for applying coatings, bands and layers to fabricate pharmaceutical dosage forms.

Suitable formulations which provide extended release profiles are well-known in the art. For example, coated slow release beads or granules ("beads" and "granules" are used interchangeably herein) in which, e.g., gaboxadol or a pharmaceutically acceptable salt thereof, alone or in combination with one or more drugs, is applied to beads, e.g., confectioners nonpareil beads, and then coated with conventional release retarding materials such as waxes, enteric coatings and the like. In embodiments, some beads incorporate one drug while other beads incorporate a different drug. In embodiments, beads can be formed in which one or more drugs are mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets. In embodiments, the ODDF is applied as a coating, a layer or a band to a capsule or tablet. In embodiments, slow release cores which are incorporated into tablets or capsules can also provide extended release profiles. For example, one or more drugs can be mixed in a substance or a mixture of substances non-absorbable from the gastrointestinal tract but capable of slow dissolution or loss of drug by leaching, and an outer drug containing ODDF layer which is applied to the core by, e.g., compression or spraying. In embodiments, extended release profiles may be provided by multiple layer tablets, each layer having different release properties. Multilayer tableting machines allow incorporation into one tablet of two or more separate layers which may be made to release one or more drugs at different rates. For example, one or more outer layers may be an ODDF, and each other layer an ERDF that exhibits different release rates. In embodiments, one or more drugs are incorporated into porous inert carriers that provide extended release profiles. In embodiments, the porous inert carriers incorporate channels or passages from which the drug diffuses into surrounding fluids. In embodiments, one or more drugs are incorporated into an ion-exchange resin to provide an extended release profile. Prolonged action can result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide an extended release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, absorbable or non-absorbable polymers may be utilized to form ERDFs. Various ERDFs including those discussed above and others that can be utilizable herein are known to those with skill in the art. See, e.g., Fu and Kao, *Expert Opin Drug Deliv.* 2010 April; 7(4): 429-444.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as gaboxadol or a pharmaceutically acceptable salt thereof at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, with respect to tablets or capsules, enteric-coated articles are examples of delayed release dosage forms. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

In embodiments, ODDFs with a delayed release formulation aspect are provided that are solid dosage forms containing medicinal substances which disintegrate rapidly, usually within a matter of seconds, when placed upon the tongue, but which also releases a drug (or drugs) at a time other than promptly after administration. Accordingly, in embodiments, modified release dosage forms herein incorporate an ODDF aspect to provide immediate release of a loading dose and then an a delayed release formulation aspect that provides a period in which there is no drug delivery followed by a period of drug delivery to provide drug levels in the blood within a desired therapeutic range for a desirable period of time in excess of the activity resulting from a single dose of the drug. In embodiments, the ODDF aspect releases drug immediately and then, after a period of delay, a delayed release formulation aspect thereafter provides a single release of drug to provide an additional period of activity. In embodiments, the ODDF aspect releases the drug immediately and then, after a period of delay, a delayed release formulation aspect thereafter provides a continuous release of drug for sustained action. In embodiments, different drugs are released together or at different times.

Delayed release dosage forms are known to those skilled in the art. For example, coated delayed release beads or granules ("beads" and "granules" are used interchangeably herein) in which, e.g., gaboxadol or a pharmaceutically acceptable salt thereof and/or other drug is applied to beads, e.g., confectioners nonpareil beads, and then coated with conventional release delaying materials such as waxes, enteric coatings and the like. In embodiments, beads can be formed in which drug is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of drug can be contained in an enterically coated capsule or tablet which releases the granules in the small intestine. In embodiments, the granules have a coating which remains intact until the coated granules reach at least the ileum and thereafter provide a delayed release of the drug in the colon. In embodiments, the entire dosage form can be enterically coated, e.g., and enteric coated tablet or capsule. Suitable enteric coating materials are well known in the art, e.g., Eudragit® coatings such methacrylic acid and methyl methacrylate polymers and others. The granules can be contained in capsules or compressed into tablets. In embodiments, the ODDF is applied as a coating, a layer or a band to the capsule or tablet. In embodiments, delayed release cores which are incorporated into tablets or capsules can also provide delayed release profiles. For example, gaboxadol or a pharmaceutically acceptable salt thereof can be mixed in a substance or a mixture of substances non-absorbable from the gastrointestinal tract but capable of slow dissolution or loss of drug by leaching, and an outer ODDF layer which is applied to the core by, e.g., compression or spraying. In embodiments, delayed release profiles may be provided by multiple layer tablets, each layer having different release properties. Multilayer tableting machines allow incorporation into one tablet of two or more separate layers which may be made to release drug at different rates after a period of delay. For example, one or more outer layers may be an ODDF, and each other layer a delayed release dosage form that exhibits different release rates. In embodiments, drug is incorporated into porous inert carriers that provide delayed release profiles. In embodiments, the porous inert carriers incorporate channels or passages from which the drug diffuses into surrounding fluids. In embodiments, drug is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, modified release pharmaceutical compositions herein include pulsatile release dosage formulations (PRDFs). Pulsatile drug release involves rapid release of defined or discrete amounts of a drug (or drugs) such as gaboxadol or a pharmaceutically acceptable salt thereof after a lag time following an initial release of drug. In embodiments, PRDFs can provide a single pulse. In embodiments, PRDFs can provide multiple pulses over time. Various PRDFs are known to those with skill in the art.

In embodiments, a PRDF can be a capsule. In embodiments, release after a lag time is provided by a system that uses osmotic pressure to cause release of a plug. In this system, gaboxadol or a pharmaceutically acceptable salt thereof is contained in an insoluble capsule shell sealed by an osmotically responsive plug, e.g., a hydrogel, which is pushed away by swelling or erosion. When the seal is broken the drug is released as a pulse from the capsule body. Contact with gastrointestinal fluid or dissolution medium causes the plug to swell, either pushing itself out of the capsule or causing the capsule to rupture after the lag-time. Position & dimensions of the plug can control lag-time. For rapid release of drug effervescent or disintegrating agents may be added. Effervescent materials can cause an increase in pressure thus aiding or causing expulsion of the plug. Examples of suitable plug material may be swellable materials coated with permeable polymer (polymethacrylates), erodible compressed polymer (HPMC, polyvinyl alcohol), congealed melted polymer (glyceryl monooleate), and enzymatically controlled erodible polymers such as pectin. In embodiments, an insoluble capsule contains multiple drug compartments separated by osmotically activated plugs. When a first plug is exposed to the environmental fluids, the first compartment opens, drug is released and the adjacent plug is exposed. The process continues until no sealed compartment are left. Lag time between pulses can be further controlled by varying the thickness of the plug and the properties of the materials from which the plug is made. More hygroscopic materials will absorb fluid faster and will swell faster. In embodiments, a membrane may be substituted for the plug. If effervescent materials are included in one or more compartments, fluids pass through the membrane by osmosis and the effervescent action and pressure increase causes the membrane to rupture, thereby releasing the drug. In embodiments, the membrane(s) are erodible and dissolve to release the contents of the compartment(s). Varying the thickness, porosity and properties of materials of the membrane can allow further control of lag time between pulses. In embodiments, a PRDF can be a tablet. In embodiments, single pulse tablets involve a core containing gaboxadol or a pharmaceutically acceptable salt thereof surrounded by one or more layers of swellable, rupturable coatings. In embodiments, a rupturable coating surrounds a swellable layer. As the swellable layer expands, it causes the rupturable coating to rupture, thereby releasing the drug from the core. Swellable materials such as hydrogels are well known. In embodiments, an inner swelling layer can contain a superdisintegrant, e.g., croscarmellose sodium, and an outer rupturable layer can be made of a polymeric porous materials such as polyethylene oxides, ethylcellulose and the like. Porous film coats of sucrose may also be suitable. In embodiments, multiple pulse tablets incorporate multiple layers surrounding a core. As a first outermost layer erodes and releases the drug contained within the layer, an underlying layer is exposed, thus releasing drug after a predetermined lag time. The process repeats until the innermost core is exposed.

In embodiments, PRDFs can incorporate ODDFs that are solid dosage forms containing medicinal substances which disintegrate rapidly, usually within a matter of seconds, when placed upon the tongue, but which also releases a drug (or drugs) in pulsatile fashion. Accordingly, in embodiments, modified release dosage forms herein can incorporate an ODDF aspect to provide immediate release of a loading dose and a PRDF aspect that provides a period in which there is no drug delivery (lag time) followed by pulsatile drug delivery to provide drug levels in the blood within a desired therapeutic range for a desirable period of time in excess of the activity resulting from a single dose of the drug. In embodiments, the ODDF aspect releases the drug immediately and then, after a period of delay, the PRDF aspect thereafter provides a single pulse release of drug to provide an additional period of activity. In embodiments, the ODDF aspect releases the drug immediately and then, after a period of delay, the PRDF aspect thereafter provides multiple pulsatile release of drug for prolonged therapeutic effect.

In embodiments, an ODDF is applied as a coating or band over a PRDF, or as a layer adjacent to a PRDF, to allow direct exposure of the ODDF to the oral cavity and consequent disintegration of the ODDF. In embodiments, the ODDF and a PRDF can be mixed in a chewable resin, e.g., gum. Those skilled in the art are familiar with techniques for applying coatings, bands and layers to fabricate pharmaceutical dosage forms.

In embodiments, the pharmaceutical compositions, including those that are modified release formulations, can include 0.1 mg to 75 mg, 0.1 mg to 70 mg, 0.1 mg to 65 mg, 0.1 mg to 55 mg, 0.1 mg to 50 mg, 0.1 mg to 45 mg, 0.1 mg to 40 mg, 0.1 mg to 35 mg, 0.1 mg to 30 mg, 0.1 mg to 25 mg, 0.1 mg to 20 mg, 0.1 mg to 15 mg, 0.1 mg to 10 mg, 0.5 mg to 75 mg, 0.5 mg to 70 mg, 0.5 mg to 65 mg, 0.5 mg to 55 mg, 0.5 mg to 50 mg, 0.5 mg to 45 mg, 0.5 mg to 40 mg, 0.5 mg to 35 mg, 0.5 mg to 30 mg, 0.5 mg to 25 mg, 0.5 mg to 20 mg, 0.5 to 15 mg, 0.5 to 10 mg, 1 mg to 75 mg, 1 mg to 70 mg, 1 mg to 65 mg, 1 mg to 55 mg, 1 mg to 50 mg, 1 mg to 45 mg, 1 mg to 40 mg, 1 mg to 35 mg, 1 mg to 30 mg, 1 mg to 25 mg, 1 mg to 20 mg, 1 mg to 15 mg, 1 mg to 10 mg, 1.5 mg to 75 mg, 1.5 mg to 70 mg, 1.5 mg to 65 mg, 1.5 mg to 55 mg, 1.5 mg to 50 mg, 1.5 mg to 45 mg, 1.5 mg to 40 mg, 1.5 mg to 35 mg, 1.5 mg to 30 mg, 1.5 mg to 25 mg, 1.5 mg to 20 mg, 1.5 mg to 15 mg, 1.5 mg to 10 mg, 2 mg to 75 mg, 2 mg to 70 mg, 2 mg to 65 mg, 2 mg to 55 mg, 2 mg to 50 mg, 2 mg to 45 mg, 2 mg to 40 mg, 2 mg to 35 mg, 2 mg to 30 mg, 2 mg to 25 mg, 2 mg to 20 mg, 2 mg to 15 mg, 2 mg to 10 mg, 2.5 mg to 75 mg, 2.5 mg to 70 mg, 2.5 mg to 65 mg, 2.5 mg to 55 mg, 2.5 mg to 50 mg, 2.5 mg to 45 mg, 2.5 mg to 40 mg, 2.5 mg to 35 mg, 2.5 mg to 30 mg, 2.5 mg to 25 mg, 2.5 mg to 20 mg, 2.5 mg to 15 mg, 2.5 mg to 10 mg, 3 mg to 75 mg, 3 mg to 70 mg, 3 mg to 65 mg, 3 mg to 55 mg, 3 mg to 50 mg, 3 mg to 45 mg, 3 mg to 40 mg, 3 mg to 35 mg, 3 mg to 30 mg, 3 mg to 25 mg, 3 mg to 20 mg, 3 mg to 15 mg, 3 mg to 10 mg, 3.5 mg to 75 mg, 3.5 mg to 70 mg, 3.5 mg to 65 mg, 3.5 mg to 55 mg, 3.5 mg to 50 mg, 3.5 mg to 45 mg, 3.5 mg to 40 mg, 3.5 mg to 35 mg, 3.5 mg to 30 mg, 3.5 mg to 25 mg, 3.5 mg to 20 mg, 3.5 mg to 15 mg, 3.5 mg to 10 mg, 4 mg to 75 mg, 4 mg to 70 mg, 4 mg to 65 mg, 4 mg to 55 mg, 4 mg to 50 mg, 4 mg to 45 mg, 4 mg to 40 mg, 4 mg to 35 mg, 4 mg to 30 mg, 4 mg to 25 mg, 4 mg to 20 mg, 4 mg to 15 mg, 4 mg to 10 mg, 4.5 mg to 75 mg, 4.5 mg to 70 mg, 4.5 mg to 65 mg, 4.5 mg to 55 mg, 4.5 mg to 50 mg, 4.5 mg to 45 mg, 4.5 mg to 40 mg, 4.5 mg to 35 mg, 4.5 mg to 30 mg, 4.5 mg to 25 mg, 4.5 mg to 20 mg, 4.5 mg to 15 mg, 4.5 mg to 10 mg, 5 mg to 75 mg, 5 mg to 70 mg, 5 mg to 65 mg, 5 mg to 55 mg, 5 mg to 50 mg, 5 mg to 45 mg, 5 mg to 40 mg, 5 mg to 35 mg, 5 mg to 30 mg, 5 mg to 25 mg, 5 mg to 20 mg, 5 mg to 15 mg, or 5 mg to 10 mg, gaboxadol or a pharmaceutically acceptable salt thereof.

In embodiments, pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, pharmaceutical compositions include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, or 20 mg gaboxadol or a pharmaceutically acceptable salt thereof or amounts that are multiples of such doses. In embodiments, pharmaceutical compositions include 2.5 mg, 5 mg, 7.5 mg, 10 mg, 15 mg, or 20 mg gaboxadol or a pharmaceutically acceptable salt thereof.

In embodiments, ODDFs include 0.05 mg, 0.1 mg, 0.25 mg, 0.5 mg, 0.75 mg, 1 mg, 1.25 mg, 1.5 mg, 1.75 mg, 2 mg, 2.5 mg, 3 mg, 3.5 mg, 4 mg, 4.5 mg, 5 mg, 7 mg, 7.5 mg, 10 mg, 12.5 mg, 15 mg, 17.5 mg, or 20 mg gaboxadol or a pharmaceutically acceptable salt thereof or amounts that are multiples of such doses.

In embodiments, ERDFs include from about 1 mg to about 100 mg gaboxadol or a pharmaceutically acceptable salt thereof. In embodiments, ERDFs include 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg gaboxadol or a pharmaceutically acceptable salt thereof.

In embodiments, delayed release dosage forms include from about 0.05 mg to about 100 mg gaboxadol or a pharmaceutically acceptable salt thereof. In embodiments, delayed release dosage forms include 0.05 mg, 0.1 mg, 0.25 mg, 0.5 mg, 0.75 mg, 1 mg, 1.25 mg, 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg gaboxadol or a pharmaceutically acceptable salt thereof.

In embodiments, PRDFs include one or more pulse providing domains having from about 0.05 mg to about 100 mg gaboxadol or a pharmaceutically acceptable salt thereof. In embodiments, PRDFs include 0.05 mg, 0.1 mg, 0.25 mg, 0.5 mg, 0.75 mg, 1 mg, 1.25 mg, 1.5 mg, 1.75 mg, 2 mg, 2.5 mg, 3 mg, 3.5 mg, 4 mg, 4.5 mg, 5 mg, 6 mg, 7 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg gaboxadol or a pharmaceutically acceptable salt thereof.

In embodiments, the respective daily amounts of melatonin and/or tasimelteon can be administered in combination with gaboxadol or a pharmaceutically acceptable salt thereof in the amounts and dosage forms discussed above. The amount of melatonin may range from 0.5 mg to 40 mg, e.g., 1 mg, 2 mg, 3 mg, 4 mg, 5 mg, 10 mg, 15 mg, 20 mg, 25 mg, 30 mg, 35 mg. The amount of tasimelteon may range from 0.5 mg to 40 mg, e.g., 5 mg, 10 mg, 15 mg, 20 mg, 25 mg, 30 mg, 35 mg. The respective daily amounts may be administered all at once or in divided doses. In embodiments, gaboxadol or a pharmaceutically acceptable salt thereof, melatonin and/or tasimelteon may be administered anywhere from one hour before bedtime to just before bedtime. It should be understood that the ranges of daily dosages discussed above include every integer and tenth of an integer between the low amount and high amount as if fully set forth herein.

In embodiments, the pharmaceutical compositions described herein may be administered once, twice, or three times daily, or every other day. In embodiments, a pharmaceutical composition described herein is provided to the patient in the evening. In embodiments, a pharmaceutical composition described herein is provided to the patient at bedtime. In embodiments, a pharmaceutical composition described herein is provided to the patient once in the evening and once in the morning. In embodiments, the total amount of gaboxadol or a pharmaceutically acceptable salt thereof administered to a subject in a 24-hour period is 1 mg to 50 mg. In embodiments, the total amount of gaboxadol or a pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 5 mg, 10 mg, or 15 mg. In embodiments, the total amount of gaboxadol or a pharmaceutically acceptable salt thereof administered to a subject in a 24-hour period is 20 mg. In embodiments, the total amount of gaboxadol or a pharmaceutically acceptable salt thereof administered to a subject in a 24-hour period is 25 mg.

In embodiments, provided herein are methods of treating non 24 sleep wake disorder including administering to a patient in need thereof a pharmaceutical composition including gaboxadol or a pharmaceutically acceptable salt thereof wherein the composition provides improvement of at least one non 24 sleep wake disorder symptom for more than 4 hours after administration of the pharmaceutical composition to the patient. In embodiments, the improvement of at least one non 24 sleep wake disorder symptom for more than 6 hours after administration of the pharmaceutical composition to the patient is provided in accordance with the present disclosure. In embodiments, improvement of at least one non 24 sleep wake disorder symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one non 24 sleep wake disorder symptom for at least e.g., 6 hours, 8 hours, 10 hours, 12 hours, 15 hours, 18 hours, 20 hours, or 24 hours after administration of the pharmaceutical composition to the patient is provided in accordance with the present disclosure. In embodiments, improvement in at least one non 24 sleep wake disorder symptom for 12 hours after administration of the pharmaceutical composition to the patient is provided in accordance with the present disclosure.

FIG. 1 shows the arithmetic mean plasma concentration-time profiles of gaboxadol following single oral doses (2.5, 5, 10, 15, and 20 mg) (see, Example 1, below) with horizontal lines Δ indicating the change between 6 and 12 hours. In embodiments, provided herein are methods of treating non 24 sleep wake disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 50% and the method provides improvement in the patient for more than 6, 8, 10, 12, 14, 16, 18, 20, 22 or 24 hours after administration. In embodiments, provided herein are methods of treating non 24 sleep wake disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 55% and the method provides improvement in the patient for more than 6, 8, 10, 12, 14, 16, 18, 20, 22 or 24 hours after administration. In embodiments, provided herein are methods of treating non 24 sleep wake disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 60% and the method provides improvement in the patient for more than 6, 8, 10, 12, 14, 16, 18, 20, 22 or 24 hours after administration. In embodiments, provided herein are methods of treating non 24 sleep wake disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating non 24 sleep wake disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 70% and the method provides improvement in the patient for more than 6, 8, 10, 12, 14, 16, 18, 20, 22 or 24 hours after administration. In embodiments, provided herein are methods of treating non 24 sleep wake disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 75% and the method provides improvement in the patient for more than 6, 8, 10, 12, 14, 16, 18, 20, 22 or 24 hours after administration.

In embodiments, provided herein are methods of treating non 24 sleep wake disorder wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating non 24 sleep wake disorder wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating non 24 sleep wake disorder wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma concentration 6 hours after administration which is less than 75% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma concentration 6 hours after administration which is less than 80% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma concentration 6 hours after administration which is less than 85% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma concentration 6 hours after administration which is less than 90% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma concentration 6 hours after administration which is less than 95% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma concentration 6 hours after administration which is less than 100% of the administered dose and provides improvement in the patient for more than 6, 8, 10, 12, 14, 16, 18, 20, 22 or 24 hours after administration.

In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement in one or more symptoms of non 24 sleep wake disorder a day after administration. In embodiments, the composition provides an in vivo plasma profile having a $C_{max}$ less than about, e.g., 250 ng/ml, 200 ng/ml 150 ng/ml, or 100 ng/ml and wherein the composition provides improvement in one or more symptoms of non 24 sleep wake disorder a day after administration.

In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng·hr/ml. In embodiments, the composition provides improvement in one or more symptoms of non 24 sleep wake disorder a day after administration. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement in one or more symptoms of non 24 sleep wake disorder a day after administration. In embodiments, the composition provides improvement in one or more non 24 sleep wake disorder symptoms for more than 6 hours after administration.

In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement symptoms of non 24 sleep wake disorder for more than, e.g., 4 hours, 6 hours, 8 hours, 10 hours, or 12 hours, after administration of the composition to the patient.

In embodiments, provided herein are methods of treating non 24 sleep wake disorder including administering to a patient in need thereof an amount of gaboxadol or a pharmaceutically acceptable salt thereof which provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof an amount of gaboxadol or a pharmaceutically acceptable salt thereof which provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof an amount of gaboxadol or a pharmaceutically acceptable salt thereof which provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof an amount of gaboxadol or a pharmaceutically acceptable salt thereof which provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof an amount of gaboxadol or a pharmaceutically acceptable salt thereof which provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof an amount of gaboxadol or a pharmaceutically acceptable salt thereof which provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 75% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 80% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 85% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 90% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 95% of the administered dose and provides improvement in the patient for more than 6, 8, 10, 12, 14, 16, 18, 20, 22 or 24 hours after administration. In embodiments, provided herein are methods of treating non 24 sleep wake disorder including administering to a patient in need thereof a pharmaceutical composition including gaboxadol or a pharmaceutically acceptable salt thereof wherein the composition provides an in vivo plasma profile having a $AUC_{6-12}$ which is less than 100% of the administered dose and provides improvement in the patient for more than 6, 8, 10, 12, 14, 16, 18, 20, 22 or 24 hours after administration.

In embodiments, provided herein are methods of treating non 24 sleep wake disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments involving administration of a first pharmaceutical composition including gaboxadol or a pharmaceutically acceptable salt thereof, and a second pharmaceutical composition including gaboxadol or a pharmaceutically acceptable salt thereof, the first and/or the second pharmaceutical compositions may be administered once, twice, or three times daily, or every other day. In embodiments, the first or the second pharmaceutical composition is provided to the patient in the evening. In embodiments, the second pharmaceutical composition includes an amount of gaboxadol that is at least one third of the amount of gaboxadol provided in the first pharmaceutical composition. In embodiments, the second pharmaceutical composition includes an amount of gaboxadol that is at least half of the amount of gaboxadol provided in the first pharmaceutical composition.

In embodiments, the first or the second pharmaceutical composition is provided to the patient once in the evening and once in the morning. In embodiments, the total amount of gaboxadol or pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 10 mg, 15 mg, or 20 mg. In embodiments, the total amount of gaboxadol or a pharmaceutically acceptable salt thereof administered to a subject in a 24-hour period is 20 mg.

In embodiments, provided herein are methods of treating non 24 sleep wake disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about, e.g., 25%, 30%, 35%, 40%, 45% or 50% less than the first pharmaceutical composition. In embodiments, the composition provides improvement in one or more symptoms of non 24 sleep wake disorder a day after administration. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating non 24 sleep wake disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptoms for more than, e.g., 6 hours, 8 hours or 12 hours after administration of the first pharmaceutical composition.

In embodiments, provided herein are methods of treating non 24 sleep wake disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments involving administration of a first pharmaceutical composition including gaboxadol or a pharmaceutically acceptable salt thereof, and a second pharmaceutical composition including gaboxadol or a pharmaceutically acceptable salt thereof, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour.

In embodiments, the first and/or the second pharmaceutical compositions contain sub therapeutic dosages. A sub therapeutic dosage of gaboxadol is an amount of gaboxadol or a pharmaceutically acceptable salt thereof that is less than the amount required for a therapeutic effect. In embodiments, a sub therapeutic dosage is an amount of gaboxadol or a pharmaceutically acceptable salt thereof that alone may not provide improvement in at least one symptom of non 24 sleep wake disorder, but is sufficient to maintain such improvement. In embodiments, the methods provide administering a first pharmaceutical composition that provides improvement in at least one symptom of non 24 sleep wake disorder, and a second composition that maintains the improvement. In embodiments, after administration of the first pharmaceutical composition, the second pharmaceutical composition may provide a synergistic effect to improve at least one symptom of non 24 sleep wake disorder. In embodiments the second pharmaceutical composition may provide a synergistic effect to improve at least one symptom of non 24 sleep wake disorder.

In embodiments, provided herein are methods of treating non 24 sleep wake disorder including administering to a patient in need thereof a pharmaceutical composition including a first pharmaceutical dosage including gaboxadol or a pharmaceutically acceptable salt thereof wherein the composition provides improvement for more than 6 hours after administration and a second pharmaceutical composition including a sub therapeutic dosage of gaboxadol or a pharmaceutically acceptable salt thereof.

Administration of the first and second pharmaceutical compositions may be separated by an interval of time to achieve long-term improvement in at least one symptom of non 24 sleep wake disorder. In embodiments, the first and second pharmaceutical composition may be administered 6 hours apart. In embodiments the first and second pharmaceutical composition may be administered 12 hours apart. In embodiments, the first and second pharmaceutical compositions may administered within, e.g., 6 hours, 12 hours, 18 hours, 24 hours etc. In embodiments, the first and second pharmaceutical compositions may administered separated by at least, e.g., 6 hours, 12 hours, 18 hours, 24 hours etc. In embodiments, improvement in at least one symptom of non 24 sleep wake disorder for more than 8 hours after administration to the patient is provided. In embodiments, improvement for more than about, e.g., 10 hours, 12 hours, 15 hours, 18 hours, 20 hours, or 24 hours after administration to the patient is provided. In embodiments, improvement in at least one symptom of non 24 sleep wake disorder for more than 8 hours after administration to the patient is provided. In embodiments, improvement for more than about, e.g., 10 hours, 12 hours, 15 hours, 18 hours, 20 hours, or 24 hours after administration to the patient is provided.

In embodiments, the first pharmaceutical composition and/or the second pharmaceutical composition include about 0.1 mg to about 40 mg gaboxadol or a pharmaceutically acceptable salt thereof. The amount of gaboxadol or a pharmaceutically acceptable salt thereof in the first pharmaceutical composition and the second pharmaceutical composition may be the same or different. In embodiments, the administration of the first and second pharmaceutical composition may provide a synergistic effect to improve at least one symptom of non 24 sleep wake disorder.

In embodiments, the first and/or the second pharmaceutical composition include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, or 3 mg to 15 mg gaboxadol or a pharmaceutically acceptable salt thereof.

In embodiments, the first and/or the second pharmaceutical composition include 5 mg to 15 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the first and/or the second pharmaceutical composition include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the first pharmaceutical compositions include 2.5 mg, 5 mg, 7.5 mg, 10 mg, 15 mg, or 20 mg gaboxadol or a pharmaceutically acceptable salt thereof. In embodiments, the second pharmaceutical compositions include 2.5 mg, 5 mg, 7.5 mg, 10 mg, 15 mg, or 20 mg gaboxadol or a pharmaceutically acceptable salt thereof.

In embodiments, the first pharmaceutical composition provides a dissolution of at least about 80% within the first 20 minutes of administration to a patient in need thereof. In embodiments, the first pharmaceutical composition provides a dissolution of at least about, e.g., 85%, 90% or 95% within the first 20 minutes of administration to a patient in need thereof. In embodiments, the first pharmaceutical composition provides a dissolution of at least 80% within the first 10 minutes of administration to a patient in need thereof.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of non 24 sleep wake disorder measured relative to at least one symptom of non 24 sleep wake disorder.

"Improvement in one or more symptoms of non 24 sleep wake disorder a day after administration" refers to improvement wherein the beneficial effect on at least one symptom lasts over a period of time, e.g., 6 hours, 12 hours, 24 hours etc. "Improvement the next day" refers to improvement which occurs a day after administration of the active agent.

Improvement in next day functioning" or "wherein there is improvement in next day functioning" refers to improvement after waking from an overnight sleep period wherein the beneficial effect of administration of gaboxadol or a pharmaceutically acceptable salt thereof, alone or in combination with one or more melatonin or tasimelteon, applies to at least one symptom or condition associated with non 24 sleep wake disorder and is discernable, either subjectively by a patient or objectively by an observer, for a period of time, e.g., 2 hours, 3 hours, 4 hours, 5 hours, 6 hours, 12 hours, 24 hours, etc. after waking.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate aspects of the disclosure herein.

"Pharmaceutically acceptable" refers to molecular entities and compositions that are "generally regarded as safe"— e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Composition", "pharmaceutical composition", "therapeutic composition", "formulation", "pharmaceutical formulation" are used interchangeably herein. "Composition", "pharmaceutical composition", "therapeutic composition", "formulation", "pharmaceutical formulation" encompass dosage forms. Dosage forms can encompass unit doses.

"Effective amount" or "therapeutically effective amount" means a dosage sufficient to alleviate one or more symptoms of a disorder, disease, or condition being treated, e.g., non 24 sleep wake disorder, or to otherwise provide a desired pharmacological and/or physiologic effect.

"Co-administered with", "in combination with", "a combination of", "administered along with", or "co-therapy", may be used interchangeably and mean that two or more agents are administered in the course of therapy. The agents may be administered together at the same time or separately in spaced apart intervals. The agents may be administered in a single dosage form or in separate dosage forms.

"Patient in need thereof" includes individuals that have been diagnosed non 24 sleep wake disorder. The methods may be provided to any individual including, e.g., wherein the patient is a neonate, infant, a pediatric patient (6 months to 12 years), an adolescent patient (age 12-18 years) or an adult (over 18 years). "Patient" and "subject" are used interchangeably herein.

EXAMPLES

The Examples provided herein are included solely for augmenting the disclosure herein and should not be considered to be limiting in any respect.

Example 1

The following Example provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailabilty of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows: Treatment A—one 2.5 mg gaboxadol capsule and 1 matching placebo capsule; Treatment B—one 5 mg gaboxadol capsule and 1 matching placebo capsule; Treatment C—one 10 mg gaboxadol capsule and 1 matching placebo capsule; Treatment D—one 15 mg gaboxadol capsule and 1 matching placebo capsule; and Treatment E—20 mg gaboxadol (two 10 mg gaboxadol capsules). Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, $C_{max}$, $T_{max}$, apparent $t_{1/2}$, cumulative urinary excretion, renal clearance, clearance, and steady-state volume of distribution, as appropriate). AUC and $C_{max}$ for gaboxadol were potency adjusted to facilitate comparison of pharmacokinetic data across studies. Table 1 provides the individual potency-adjusted pharmacokinetic parameters of gaboxadol following single oral doses (2.5, 5, 10, 15, and 20 mg).

TABLE 1

Pharmacokinetic parameters for gaboxadol following oral and IV administration

| Parameter | Geometric Mean (N = 10) | | | | | | |
|---|---|---|---|---|---|---|---|
| | 2.5 mg | 5 mg | 10 mg Oral | 10 mg I.V. | 15 mg | 20 mg | Slope (90% CI) [††] |
| $AUC_{0-\infty}$ (ng · hr/mL) | 90 | 171 | 346 | 380 | 539 | 669 | 0.98 (0.95, 1.01) |
| $C_{max}$ (ng/mL)[†] | 61 | 110 | 232 | 212 | 382 | 393 | 0.95 (0.88, 1.02) |
| $T_{max}$ (hr)[‡] | 0.5 | 0.6 | 0.5 | — | 0.5 | 0.6 | |
| Apparent $t_{1/2}$ (hr)[§] | 1.5 | 1.5 | 1.6 | 1.5 | 1.5 | 1.6 | |
| CL/F (mL/min)[ϑ] | 461 | 488 | 476 | 438 | 469 | 499 | |
| $F_e$ (%) | 43 | 45 | 53 | 53 | 50 | 53 | |
| $CL_R$ (mL/min) | 196 | 222 | 250 | 208 | 234 | 265 | |
| F (%) (90% CI)[#] | | | | 92% (0.86, 0.97) | | | |

[†]$C_{ooi}$ (ng/mL) for 10 mg. I.V.

[‡]Median.

[§]Harmonic Mean.

[ϑ]CL (mL/min) for 10 mg IV.

[#]Bioavailability relative to 10 mg I.V. reference based on pooled dose-adjusted (to 10 mg) oral $AUC_{0-\infty}$ values.

[††] Dose proportionality assessment of oral treatments only.

Figure 2:
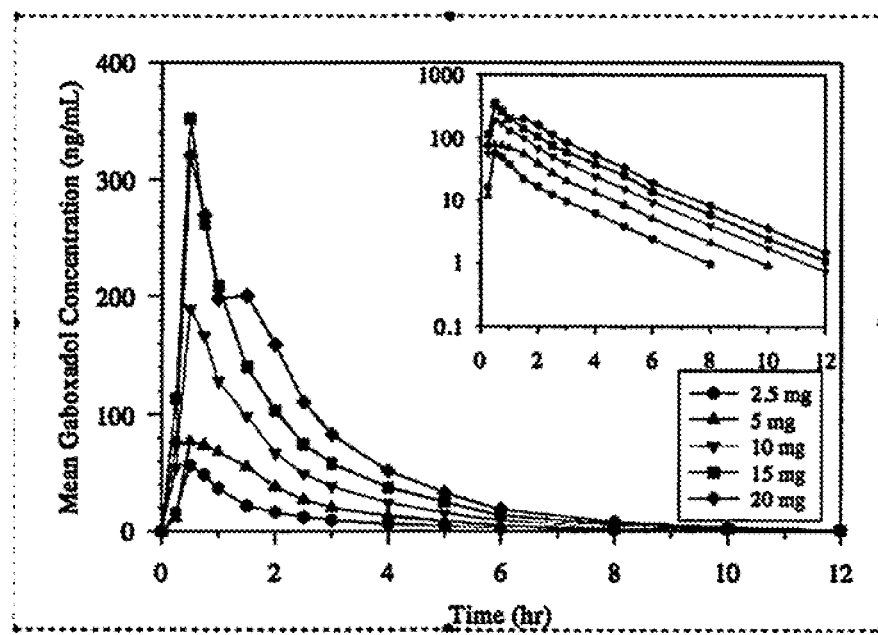
FIG. 2 shows the arithmetic mean plasma concentration-time profiles of gaboxadol following single oral doses (2.5, 5, 10, 15, and 20 mg) as described in Example 1.

FIG. 2 shows the arithmetic mean plasma concentration-time profiles of gaboxadol following single oral doses (2.5, 5, 10, 15, and 20 mg). The bioavailability of gaboxadol is approximately 92%. Plasma $AUC_{0-\infty}$ and $C_{max}$ of gaboxadol show dose proportional increases and appear to be linear over the entire dose range examined, from of 2.5 to 20 mg. The time to peak plasma concentrations ($T_{max}$ 30-60 min) and the half-life (t½ of 1.5 h) for gaboxadol appear to be independent of dose across the gaboxadol dose range of 2.5 to 20 mg. The excretion of gaboxadol is mainly via urine, where 96.5% of the dose is recovered; 75% is recovered within 4 hours after administration.

Example 2

Assessment of Residual Effects Resulting from Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg. All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit symbol substitution test (DSST), Tracking, Memory tests, Body Sway, and Leeds Sleep Evaluation Questionnaire).

Example 3

Prospective Assessment of the Efficacy of Gaboxadol in Patients with Non 24 Sleep Wake Disorder This study is designed to determine whether gaboxadol leads to an improvement in non 24 sleep wake disorder. A primary objective of this study will be to evaluate the safety, tolerability and efficacy from Baseline to Week 6 and Week 12 of gaboxadol in adult subjects with non 24 sleep wake disorder across different dose levels and in two dosing schedules. The study will have two phases: a pre-randomization phase followed by either a randomization phase or an open-label extension (OLE). The pre-randomization phase encompasses a screening visit where subject's initial eligibility will be evaluated, a circadian period (τ) estimation segment, and a variable-length in-phase transition segment in which subjects will wait to start treatment until their circadian phase is aligned with their target bedtime. Subjects that meet all entry criteria for the study will enter the randomization phase. During the randomization phase, subjects will be asked to take gaboxadol or placebo approximately 1 hour prior to their target bedtime in a double-masked fashion. The following dosing schedules may also be tested against placebo: (1) Once daily (o.d.): An evening dose, titrated to the target dose of 15 mg unless not tolerated; and (2) Twice daily (b.i.d.): Evening and morning doses titrated to the target doses of 15 mg evening dose and 10 mg morning dose unless not tolerated.

The Safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine).

Another objective of this study can include the identification of a set of parameters that may best characterize the efficacy of gaboxadol in non 24 sleep wake disorder subjects for subsequent efficacy trials. These tests may be administered at four full day site visits (Screening, Baseline, Interim and End of Treatment) by an appropriately trained professional to provide the test to an adult non 24 sleep wake disorder patient. Assessments may be based, in part, on patient's perception of symptoms.

This study can include three treatment groups. For example, a total of approximately 75 subjects can be enrolled and at the completion of the study, there may be approximately 25 subjects in each of the three treatment groups: 1) single evening dose in proximity to bedtime 2) morning and evening dose and 3) placebo. All subjects may be up-titrated to the target dose unless this target dose is not tolerated (titration conventions described below). All subjects may receive treatment for a maximum of 12 weeks at their optimal tolerated dose.

Doses may be progressively increased in 5 mg increments (active or placebo) to a target dose of 3 capsules evening dose in schedule A and B, and 2 capsules morning dose in schedule B. Each dose escalation may be performed after adequate tolerability has been assessed by caregiver and investigator. For example, treatment initiation at Day 1 with 1 capsule (active (Act) or placebo (Plc)) in the evening. Then target up-titration may begin at Day 3 (window+2 days): If no adverse event (AE) related to the study drug is observed by caregiver and/or the investigator, another capsule (active or placebo) is added in the evening. Again at Day 7 (window+2 days), Day 10 (window+2 days and Day 14 (window+2 days) if no AE related to the study drug is observed by caregiver and/or the investigator, another capsule (active or placebo) may be added in the morning. Table II below provides a graphic illustration of the titration schedule.

TABLE II

Titration Schedule

| Schedule/Time | | Days 1 to 2 | Days 3 to 6 | Days 7 to 9 | Days 10 to 13 | Day 14* |
|---|---|---|---|---|---|---|
| Schedule A | Evening | 5 mg 1 Capsule | 10 mg 2 Capsules | 15 mg 3 Capsules | 15 mg 3 Capsules | 15 mg 3 Capsules |
| | Morning | None | None | None | Placebo 1 Capsule | Placebo 2 Capsules |
| Schedule B | Evening | 5 mg 1 Capsule | 10 mg 2 Capsules | 15 mg 3 Capsules | 15 mg 3 Capsules | 15 mg 3 Capsules |
| | Morning | None | None | None | 5 mg 1 Capsule | 10 mg 2 Capsules |
| Schedule C | Evening | Placebo 1 Capsule | Placebo 2 Capsules | Placebo 3 Capsules | Placebo 3 Capsules | Placebo 3 Capsules |
| | Morning | None | None | None | Placebo 1 Capsule | Placebo 2 Capsules |

*To end of study treatment period

Slowed up-titration or delayed up-titration will be acceptable if tolerability does not allow immediate further dose-escalation at any of the above detailed days (3, 7, 10, 14). Down-titration in the case tolerability is not acceptable (e.g., somnolence, dizziness, change in behavior) after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (2 capsules in the morning and 3 in the evening) the subject may be kept stable until End of Treatment visit (week 12) unless intolerability requires down-titration.

All subjects will be screened for participation in the study up to 28 days prior to the first dose administration. Inclusion criteria may include one or more of the following: (1) Age ≥18 years, ≤40 years; (2) Must possess a clinical diagnosis of non 24 sleep wake disorder. Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Primary outcome measures: 1) The proportion of entrained patients. Entrainment is a measure of synchronization of the master body clock to the 24-hour day. The circadian period ($\tau$) will be calculated using urinary aMT6s collected over four 48 hour periods, collected approximately 1 week apart for 4 separate weeks. Entrainment may be defined as having a post-baseline $\tau$ value less than 24.1 and a 95% CI that includes 24.0.

2) A step-down primary endpoint assesses the proportion of patients who have a clinical response (entrainment at month 1 plus clinical improvement, measured by the Non-24 Clinical Response Scale. Clinical response may be defined as the coincident demonstration of entrainment (aMT6) and a score ≥3 on the Non-24 Clinical Response Scale (N24CRS). N24CRS measures improvement in sleep-wake measures and overall functioning (LQ-nTST, UQ-dTSD, MoST and CGI-C). Each assessment will be scored as a 1 or 0.

Secondary outcome measures: 1) Safety will be assessed by monitoring and recording all Adverse Events (AE) and serious adverse events (SAE), regular monitoring of hematology, blood chemistry, and urine values, regular measurement of vital signs and the performance of a physical examination and an ECG.

2) Proportion of Patients Entrained as Assessed by Urinary Cortisol. The circadian period ($\tau$) will be calculated using urinary cortisol collected over four 48 hour periods, approximately 1 week apart for 4 separate weeks, during the screening and month 1 of the randomization phase of the trial. Entrainment may be defined as having a post-baseline $\tau$ value less than 24.1 and a 95% CI that includes 24.0.

3) Average Clinical Global Impression of Change (CGI-C). CGI-C scores will range from 1 (very much improved) to 7 (very much worse). The average post-randomization score will be obtained for each patient by averaging the last 2 scheduled assessments (Day D112 and Day D183). A lower number will indicate improvement.

4) Proportion of Responders With a Combined Sleep/Wake Response for LQ-nTST (≥90 Minutes) and UQ-dTSD (≤90 Minutes). The sleep/wake response represents measurement of the combined improvement in the nighttime sleep duration and daytime sleep duration. Individuals that have an improvement in nighttime sleep and daytime sleep, defined as an increase of 90 minutes or more in the lower quartile of subjective nighttime total sleep time (LQ-nTST) and a decrease of 90 minutes or more in the upper quartile of daytime total sleep duration (UQ-dTSD) will be considered to be a responder.

5) Average Lower Quartile of Nights of Nighttime Total Sleep Time (LQ-nTST). LQ-nTST measures the difference in average nighttime sleep during the patient's worst 25% of nights (shortest total nighttime sleep) between the randomized phase and the screening phase (~6 weeks). A higher number will indicate improvement.

Those skilled in the art will recognize, or be able to ascertain using no more than routine experimentation, many equivalents to the specific embodiments described herein. Such equivalents are intended to be encompassed by the claims.

What is claimed is:

1. A method of treating non 24 hour sleep wake disorder comprising administering to a patient in need thereof about 0.05 mg to about 30 mg gaboxadol or a pharmaceutically acceptable salt thereof, wherein the method provides improvement in at least one symptom of the 24 hour sleep wake disorder selected from the group consisting of irregular sleep patterns, irregular circadian rhythms, apraxia, cognitive dysfunction, difficulties concentrating, confusion, depressed mood, diarrhea, nausea, hair loss, headache, impaired balance, photosensitivity, joint pain, ataxia, menstrual irregularities, muscle pain, suicidal thoughts, weight gain, and hallucinations.

2. The method of claim 1, wherein the improvement is provided for at least 6 hours after administration.

3. The method of claim 1, wherein the patient is administered a composition comprising about 1 mg to about 15 mg gaboxadol or a pharmaceutically acceptable salt thereof.

4. The method of claim 1, wherein the in vivo plasma profile of gaboxadol in the patient 6 hours after administration of the gaboxadol or pharmaceutically acceptable salt thereof is reduced by more than 50%.

5. The method of claim 1, wherein the $AUC_{6-12}$ of gaboxadol in the patient 6 hours after administration of the gaboxadol or pharmaceutically acceptable salt thereof is less than 75% of the administered dose.

6. The method of claim 1, wherein the apraxia is selected from the group consisting of ideomotor apraxia, kinetic apraxia, limb apraxia, and verbal apraxia.

7. The method of claim 2, wherein the method provides improvement in the patient for more than 6 hours.

8. The method of claim 2, wherein the method provides improvement in the patient for at least 12 hours.

9. The method of claim 1, further comprising administering melatonin or tasimelteon to the patient.

10. A method of treating non 24 hour sleep wake disorder comprising administering to a patient in need thereof gaboxadol or a pharmaceutically acceptable salt thereof wherein the method provides an in vivo plasma profile of gaboxadol comprising a $C_{max}$ less than about 400 ng/ml.

11. A method of treating non 24 hour sleep wake disorder comprising administering to a patient in need thereof gaboxadol or a pharmaceutically acceptable salt thereof wherein the method provides an in vivo plasma profile of gaboxadol comprising a $AUC_{6-12}$ of less than about 900 ng·hr/ml.

* * * * *